(12) United States Patent
Iaizzo et al.

(10) Patent No.: US 8,332,035 B2
(45) Date of Patent: Dec. 11, 2012

(54) PACING METHOD

(75) Inventors: Paul A. Iaizzo, White Bear Lake, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 472 days.

(21) Appl. No.: 12/435,987

(22) Filed: May 5, 2009

(65) Prior Publication Data
US 2009/0276000 A1    Nov. 5, 2009

Related U.S. Application Data

(63) Continuation of application No. 10/782,420, filed on Feb. 19, 2004, now Pat. No. 7,529,584.

(51) Int. Cl.
*A61N 1/362* (2006.01)
(52) U.S. Cl. .............................. 607/27; 607/28; 600/510
(58) Field of Classification Search ................... 600/510, 600/517; 607/9, 27, 28
See application file for complete search history.

(56) References Cited

U.S. PATENT DOCUMENTS

| | | | |
|---|---|---|---|
| 4,026,303 A | 5/1977 | Babotai | |
| 4,149,542 A | 4/1979 | Thoren | |
| 4,337,776 A | 7/1982 | Daly et al. | |
| 4,453,551 A | 6/1984 | Anderson et al. | |
| 4,506,680 A | 3/1985 | Stokes | |
| 4,562,846 A | 1/1986 | Cox et al. | |
| 4,577,642 A | 3/1986 | Stokes | |
| 4,603,704 A | 8/1986 | Mund et al. | |
| 4,606,118 A | 8/1986 | Cannon et al. | |
| 4,677,989 A | 7/1987 | Robblee | |
| 4,711,251 A | 12/1987 | Stokes | |
| 4,773,433 A | 9/1988 | Richter et al. | |
| 4,784,160 A | 11/1988 | Szilagyi | |
| 4,784,161 A | 11/1988 | Skalsky et al. | |
| 4,819,661 A | 4/1989 | Heil, Jr. et al. | |
| 4,819,662 A | 4/1989 | Heil, Jr. et al. | |
| 5,425,363 A | 6/1995 | Wang | |
| 5,443,492 A | 8/1995 | Stokes et al. | |
| 5,487,758 A | 1/1996 | Hoegnelid et al. | |
| 5,709,644 A | 1/1998 | Bush | |
| 5,728,140 A | 3/1998 | Salo et al. | |
| 5,843,148 A | 12/1998 | Gijsbers et al. | |

(Continued)

FOREIGN PATENT DOCUMENTS

EP    0 414 233 B1    10/1996

(Continued)

OTHER PUBLICATIONS

Becker et al., "Proximal Atrioventricular Bundle, Atrioventricular Node, and Distal Atrioventricular Bundle are Distinct Anatomic Structures with Unique Histological Characteristics and Innervation," *Circulation*, Feb. 13, 2001; 103(b):e31.

(Continued)

*Primary Examiner* — George Evanisko
(74) *Attorney, Agent, or Firm* — Carol F. Barry

(57) ABSTRACT

A method for delivering physiological pacing includes selecting an electrode implant site for sensing cardiac signals, which is in proximity to the heart's intrinsic conduction system, where pacing stimulation results in a rhythm breaking out at an intrinsic location, and selected in response to a ratio of sensed P-wave amplitude to sensed R-wave amplitude.

20 Claims, 25 Drawing Sheets

U.S. PATENT DOCUMENTS

| | | | |
|---|---|---|---|
| 5,987,746 A | 11/1999 | Williams | |
| 6,066,165 A | 5/2000 | Racz | |
| 6,192,280 B1 | 2/2001 | Sommer et al. | |
| 6,301,492 B1 | 10/2001 | Zonenshayn | |
| 6,415,187 B1 | 7/2002 | Kuzma et al. | |
| 6,473,649 B1 | 10/2002 | Gryzwa et al. | |
| 6,556,874 B2 | 4/2003 | Audoglio | |
| 6,643,546 B2 | 11/2003 | Mathis et al. | |
| 6,768,923 B2 | 7/2004 | Ding et al. | |
| 7,529,584 B2 * | 5/2009 | Laske et al. | 607/9 |
| 2002/0133199 A1 | 9/2002 | MacDonald et al. | |
| 2003/0105492 A1 | 6/2003 | Ding et al. | |

FOREIGN PATENT DOCUMENTS

EP  0 795 343 A2  9/1997

OTHER PUBLICATIONS

Bharati et al., "The Conduction System of the Swine Heart," *Chest*; 1991; 100:207-212.

Bharati, Saroja, "Anatomy of the Atrioventricular Conduction System," *Circulation*, Mar. 27, 2001;13(2):e63-e64.

Chinchoy et al., "Isolated Four-Chamber Working Swine Heart Model," *Ann. Thorac. Surg.*, 2000; 70:1607-14.

Deshmuk et al., "Permanent, Direct His-Bundle Pacing: A Novel Approach to Cardiac Pacing in Patients With Normal His-Purkinje Activation," *Circulation*, Feb. 29, 2000; 101(8):869-877.

Ho et al., "The Architecture of the Atrioventricular Conduction Axis in Dog Compared to Man—Its Significance to Ablation of the Atrioventricular Nodal Approaches," *Cardiovascular Electrophysiology*, 1995; 6:26-39.

International Search Report for PCT/US03/31041 dated Jul. 19, 2004; 10 pgs.

Karpawich et al., "Chronic Epicardial His Bundle Recordings in Awake Nonsedated Dogs: A New Method," *American Heart Journal*, 1983; 105:16-21.

Karpawich et al., "Septal His-Purkinje Ventricular Pacing in Canines: A New Endocardial Electrode Approach," *PACE*, 1992; 15:2011-2015.

Karpawich et al., "Altered Cardiac Histology Following Apical Right Ventricular Pacing in Patients with Congenital Atriventricular Block," *PACE*, 1999; 22:1372-1377.

Kucera et al., "Mechanistic Insights Into Very Slow Conduction in Branching Cardiac Tissue—A Model Study," *Circulation Research*, 2001; 89:799-806.

Mazgalev et al., "Anatomic-Electrophysical Correlations Concerning the Pathways for Atrioventricular Conduction," *Circulation*, Jun. 5, 2001; 103(22):2660-2667.

Racker et al., "Proximal Atrioventricular Bundle, Atrioventricular Node, and Distal Atrioventricular Bundle are Distinct Anatomic Structures with Unique Histological Characteristics and Innervation," *Circulation*, 2000; 101:1049-1059.

Scheinman et al., "Long-Term His-Bundle Pacing and Cardiac Function," *Circulation*, Feb. 29, 2000; 101(8):836.

Williams et al., "Selective Versus Non-Selective His Bundle Pacing," *Cardiovascular Research*, 1976; 10:91-100.

Zhang et al., "His Electrogram Alternans Reveal Dual-Wavefront Inputs Into and Longitudinal Dissociation Within the Bundle of His," *Circulation*, 2001; 104:832-838.

* cited by examiner

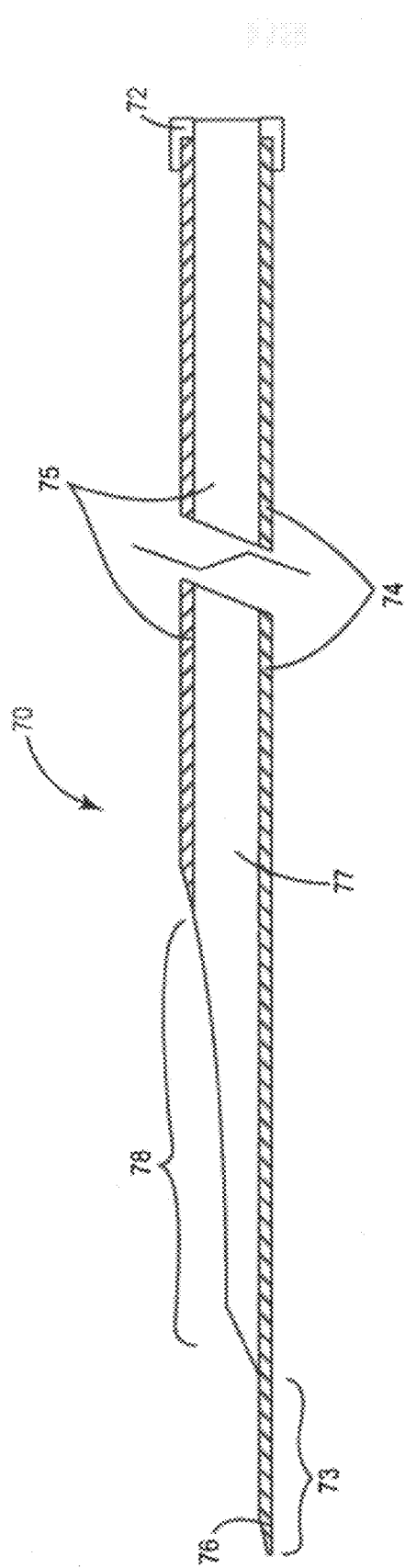

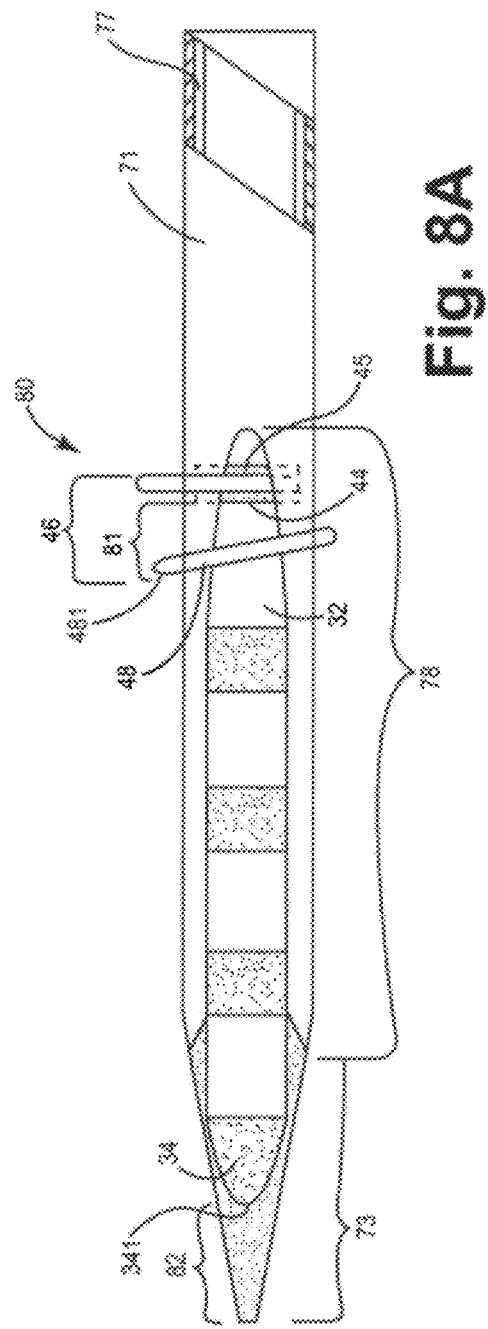
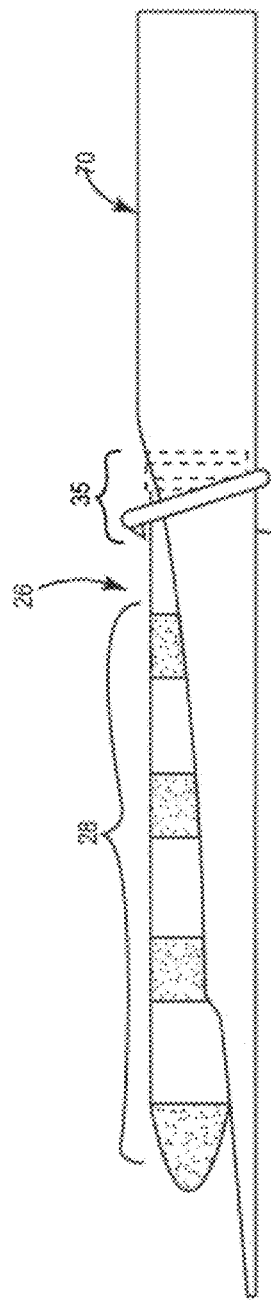
Fig. 8A
Fig. 8B

PACING METHOD

REFERENCE TO RELATED APPLICATIONS

This application is filed as a continuation of application Ser. No. 10/782,420, filed on Feb. 19, 2004.

FIELD OF THE INVENTION

The present invention generally relates to implantable medical devices, and more particularly to methods for improved physiological pacing.

BACKGROUND OF THE INVENTION

Various types of pacing leads have been developed for endocardial introduction into different chambers of a patient's heart, typically a right ventricle, right atrial appendage, or coronary sinus. These flexible leads are usually constructed having an outer polymeric sheath encasing one or more electrical conductors. The conductors may be arranged coaxially or co-radially and are insulated from one another. A distal end of each conductor is coupled to one or more electrodes while a proximal end of each conductor is coupled to a contact of a connector that is in turn coupled to an implantable pulse generator (IPG). The distal end of the lead is implanted to be positioned within the heart so that the electrodes may deliver pacing therapy by both sensing electrical activity of the heart muscle and stimulating the heart muscle.

The IPG may be a single chamber atrial pacemaker, a single chamber ventricular pacemaker, or a dual chamber pacemaker. The leads sense electrical activity in the heart and deliver stimulation pulses from the IPG when spontaneous electrical activity ceases, accelerates, or becomes disorganized. In the conventional single chamber atrial system, pacing therapy is delivered from lead electrodes located in the right atrial appendage. In the conventional single chamber ventricular system, pacing therapy is delivered from lead electrodes located in the right ventricular (RV) apex. In a conventional dual chamber system, leads function in both the right atrium and right ventricle. A lead implanted in the right atrium can provide pacing therapy to preserve both atrial-ventricular synchronization and the normal ventricular activation and contraction patterns. However, pacing from the atrial appendage is ineffective if the conduction between the atria and ventricles is blocked.

Automatic electrical impulses from the sinoatrial (SA) node, located in the anterosuperior wall of the right atrium, travel through the walls of the right and left atria to the atrioventricular (AV) node. At the AV node, the electrical impulse is delayed to allow time for the atria to complete their contraction before the ventricles are activated. The delay allows the ventricles to adequately fill with blood prior to contraction. The AV node is located in the septal wall of the right atrium immediately posterior to the tricuspid valve. After passing through the AV node, the impulse travels rapidly through the atrioventricular bundle, also known as the bundle of His, and spreads down the interventricular septum, via the right and left bundle branches, and then throughout the walls of the ventricles, via the Purkinje fibers. The bundle of His extends from the AV node within the fibrous tissue between the tricuspid and mitral valves, where the atrioventricular septum joins the interventricular septum, and into the interventricular septum. Localized ischemia, inflammation, congenital defects, or compression of the AV node or the bundle of His can cause a block of electrical conduction between the atria and ventricles. Permanent block may also be caused by ablation to prevent conduction as a treatment for atrial fibrillation in some patients. Ventricular pacing is the standard means employed to bypass the block between the atria and ventricles.

Ventricular pacing is typically delivered from a lead's electrodes implanted in the apex of the right ventricle. Stimulation from this site is counter to the heart's natural operation. When the electrodes, located in the apex, deliver the electrical pulse the myocardial cells local to the apex begin to contract. The electrical signal then expands, relatively slowly compared to the heart's natural contraction, upward and outward until the ventricles fully contract. Therefore, ventricular pacing sends an electrical impulse that moves from the bottom to the top of the ventricles, and from the right to the left ventricle, causing an unnatural ventricular contraction pattern.

Some studies have put forth the proposition that significant problems are associated with pacing from the ventricular apex. It has been speculated that such non-physiological pacing can cause ventricular wall abnormalities, inferior localized myocardial perfusion defects and mitral regurgitation. In addition, pacing from the ventricular apex has been alleged to create myofibrilar disarray and fatty deposits throughout the ventricles. Myofibrilar disarray and fatty deposits have been associated with congestive heart failure.

Therefore, what is needed is a method and apparatus for providing physiological pacing. Physiological pacing is defined herein as stimulation of the intrinsic conduction system of the heart that preserves a natural contraction pattern of the heart.

BRIEF DESCRIPTION OF THE DRAWINGS

FIG. 7B is a cross-section side view of the piercing tool.

FIGS. 8A-B are a top plan view and side elevation view, respectively of a distal portion of a physiological pacing lead delivery system.

DETAILED DESCRIPTION OF THE INVENTION

Figure 1:
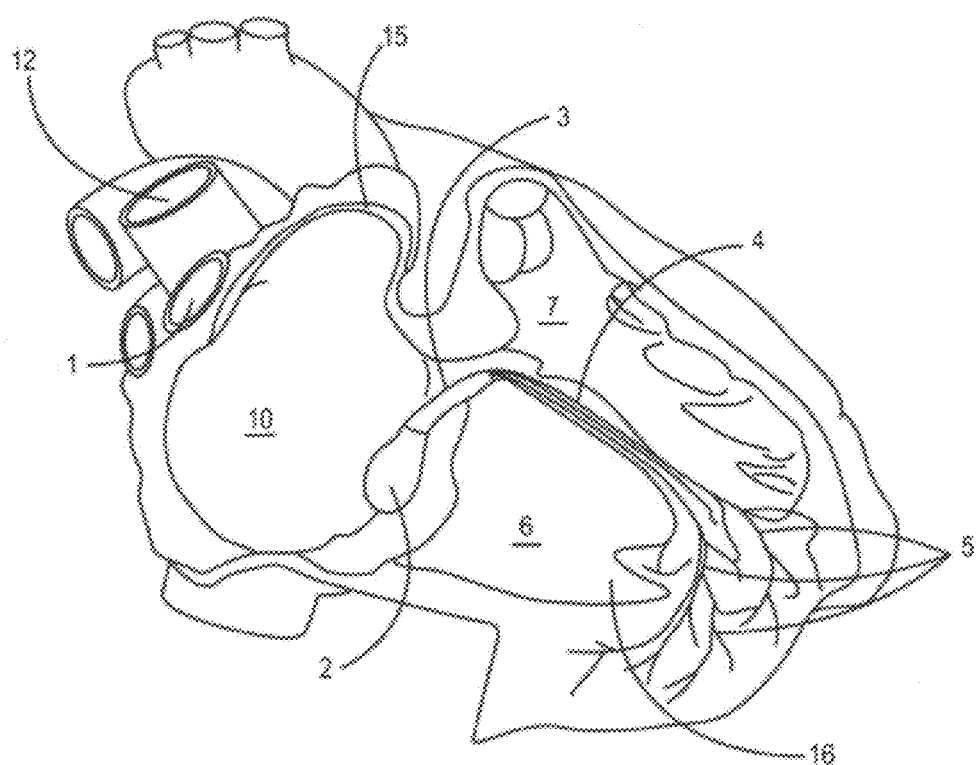
FIG. 1 is a schematic diagram of a right side of a heart having an anterior-lateral wall peeled back to present a portion of a heart's intrinsic conduction system and chambers of a right atrium and ventricle.

FIG. 1 is a schematic diagram of a right side of a heart having an anterior-lateral wall peeled back to present a portion of a heart's intrinsic conduction system and chambers of a right atrium 10 and a right ventricle 6. Pertinent elements of the heart's intrinsic conduction system, illustrated in FIG. 1, include a sinoatrial (SA) node 1, an atrioventricular node 2, a bundle of His 3, a right bundle branch 4, and Purkinje fibers 5. SA node 1 is shown at a junction between a superior vena cava 12 and right atrium (RA) 10. An electrical impulse starting at SA node 1 travels rapidly through RA 10 and a left atrium 8 (FIG. 15) to AV node 2. At AV node 2, the impulse slows to create a delay before passing on through a bundle of His 3, which branches, in an interventricular septum 7, into a right bundle branch 4 and a left bundle branch 84 (FIG. 15) and then, apically, into Purkinje fibers 5. Following the delay, the impulse travels rapidly throughout right ventricle (RV) 6 and a left ventricle (not shown). Flow of the electrical impulse described herein creates an orderly sequence of atrial and ventricular contraction and relaxation to efficiently pump blood through the heart. When a portion of the heart's intrinsic conduction system becomes damaged, efficient pumping is compromised. Typically, a patient, whose SA node 1 has become damaged, may have a pacemaker system implanted wherein lead electrodes are placed in an atrial appendage 15. The lead electrodes stimulate RA 10 downstream of damaged SA node 1 and the stimulating pulse travels on to AV node 2, bundle of His 3, and Purkinje fibers 5 to restore physiological contraction of the heart. However, if a patient has a damaged AV node 2, pacing in atrial appendage 15 will not be effective, since it is upstream of a block caused by the damage. Typically, this patient may have a pacemaker system implanted wherein lead electrodes are placed in an RV apex 16. RV apex 16 has been an accepted site for electrode placement since it is relatively easy to engage a lead electrode at this site and pacing from this site has been proven safe and effective. More recently questions have been raised regarding long-term effects of pacing from RV apex 16, since conduction from this site does not spread as rapidly as, and is contrary in direction to natural conduction.

Figure 2:
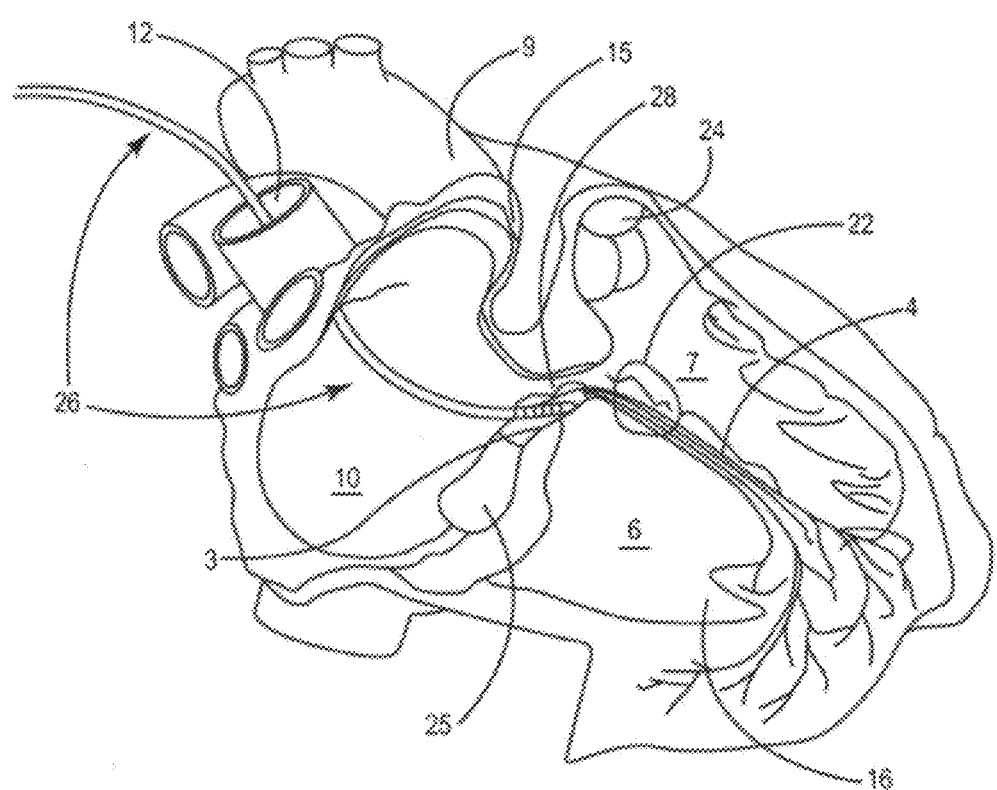
FIG. 2 is a schematic diagram of a right side of a heart, similar to FIG. 1, in which an alternative site for pacing is depicted.

FIG. 2 is a schematic diagram of a right side of a heart, similar to FIG. 1, in which an alternative site for pacing is depicted. According to the present invention and illustrated in FIG. 2, a physiological pacing lead 26 having an electrode array 28 is implanted in RA 10, embedded near an annulus of tricuspid valve 25 in fibrous tissue containing bundle of His 3. Any electrode or combination of electrodes in array 28, in relative proximity with healthy conductive fibers of bundle of His 3, may be selected for operation of physiological pacing lead 26. Bundle of His 3 can be accessed endocardially, as illustrated in FIG. 2, transvenously via a subclavian entry (not shown) and through superior vena cava 12 to RA 10, or from an epicardial entry point near right atrial appendage 15 at a base of an aorta 9. It should be noted that physiological pacing lead 26 may be implanted such that electrode array 28 is embedded in relative proximity to any other portion of the heart's intrinsic conduction system, such as right bundle branch 4 or left bundle branch (not shown) in the interventricular septum near a site 22.

Figure 3:
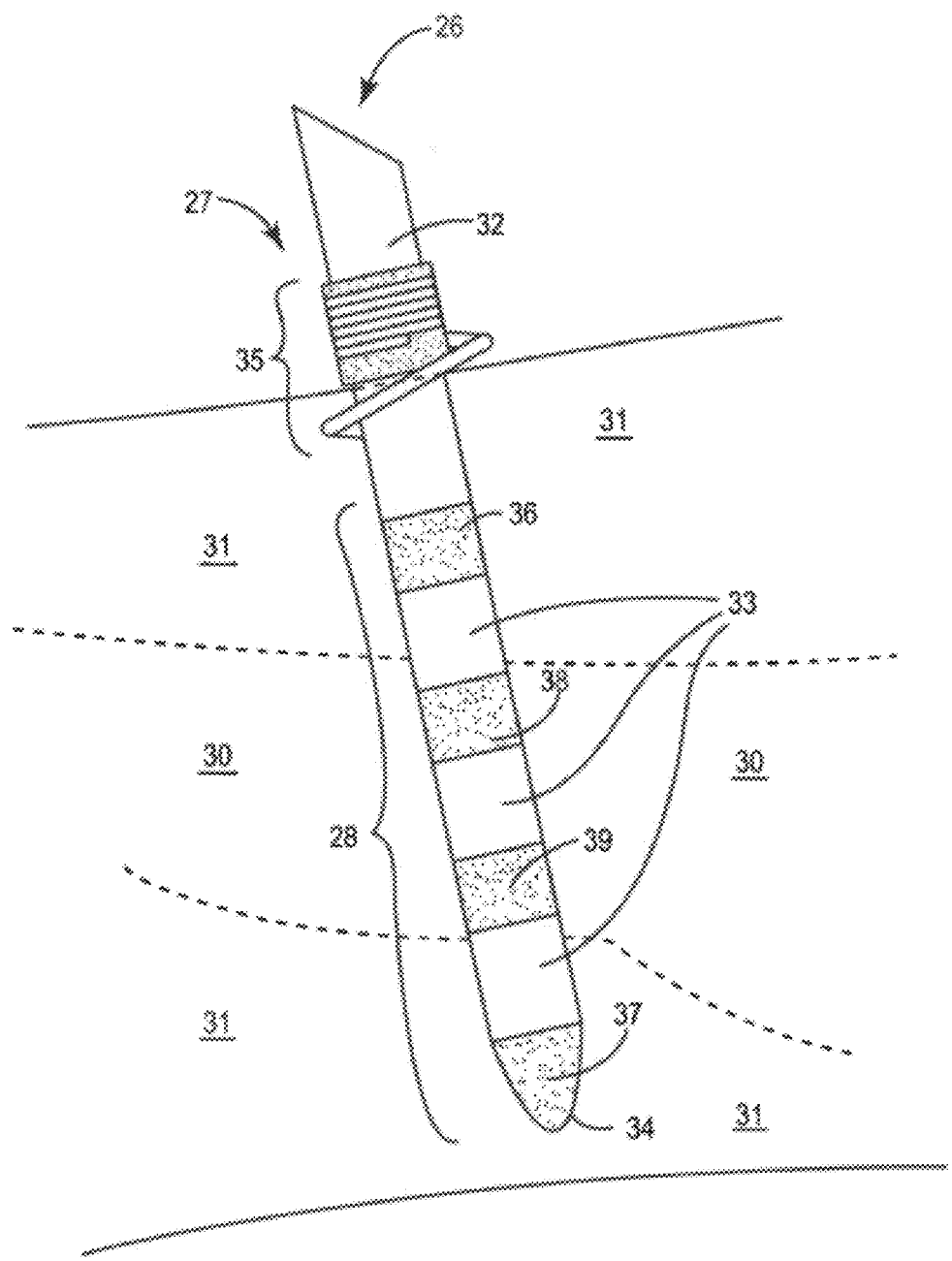
FIG. 3 is a schematic diagram of an electrode array of a physiological pacing lead implanted in a section of tissue enlarged from FIG. 2.

FIG. 3 is a schematic diagram of electrode array 28 of physiological pacing lead 26 embedded in a section of tissue enlarged from FIG. 2. The FIG. 2 schematic is a simplified two-dimensional illustration of an interface between elements at distal end 27 of lead 26 and a conductive bundle of His zone 30 (between dashed lines) and fibrous zones 31. Electrode array 28 includes an alternating series of electrodes 36, 37, 38, 39 separated by corresponding spacer elements 33 coaxially positioned about distal end 27 of a lead body 32. A most proximal electrode 36 and a most distal electrode 37 are on either side of intermediate electrodes 38, 39 whose number may be two, as shown, or more. As illustrated in FIG. 3, most distal electrode 37, terminating electrode array 28, includes a tapered tip 34 to facilitate insertion into tissue. Alternately, a tapered tip may be an element separate from, but joined to most distal electrode 37. A fixation element 35 is coupled to lead body 32, proximal to electrode array 28.

FIG. 3 illustrates electrode array 28 embedded so that intermediate electrodes 38, 39 are within conductive bundle of His zone 30 while most proximal electrode 36 and most distal electrode 37 are within fibrous zone 31. In the illustrated case, one or a pair of electrodes 36, 37, 38, 39 may be selected for pacing bundle of His zone 30, but intermediate electrodes 38, 39 may be preferred since they are in close proximity to His zone 30 and will likely require a lower energy to stimulate intrinsic conduction system via His zone 30. Because margins of bundle of His zone 30 (dashed lines) will vary from patient to patient, another case may present bundle of His zone 30 shifted up or down and, or narrower such that different electrodes, within electrode array 28, than those shown in FIG. 3 may be in closest proximity with bundle of His zone 30.

Figure 4A:
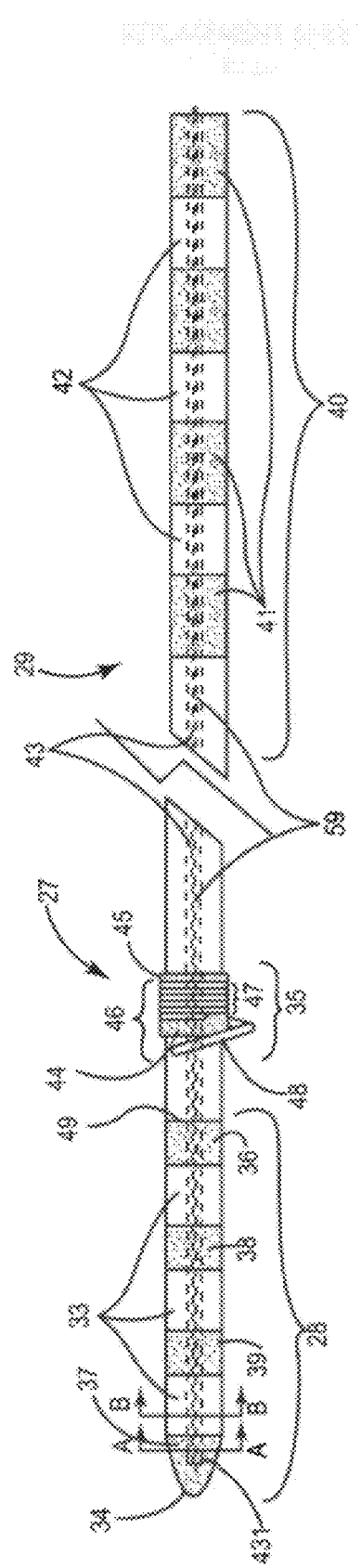
FIG. 4 is a side plan view of the physiological pacing lead according to the present invention.
FIGS. 4B-C are radial section views from FIG. 4A.
FIG. 4D is a distal end view from FIG. 4A.

FIG. 4A is a side plan view of physiological pacing lead 26 according to a preferred embodiment of the present invention. As illustrated in FIG. 4A, electrode array 28 is disposed about lead body 32 at distal end 27 and a connector assembly 40 is disposed at a proximal end 29. Fixation element 35, having a collar 45 and a helical hook 46, is disposed about and joined to lead body 32 proximal to electrode array 28. Connector assembly 40 includes an alternating series of connector contacts 41 and isolation zones 42 coaxially positioned about lead body 32. In a preferred embodiment, lead body 32 has a maximum diameter between approximately 0.040 inches and 0.070 inches.

Electrodes 36, 37, 38, 39 of electrode array 28 are preferably formed from a platinum alloy and may have a porous surface structure. The porosity is intended to reduce the foreign body response, stimulation thresholds, signal source impedance, and polarization. Although platinum is preferred other materials may also be used including but not limited to such materials as palladium, titanium, tantalum, rhodium, iridium, carbon, vitreous carbon and alloys, oxides and nitrides of such metals or other conductive or even semiconductive materials. Of course, some materials are incompatible with others and may not be effectively used together. The limitations of specific materials for use with others are well known in the art. Examples of acceptable electrode materials and associated fabrication techniques employed to achieve the micro-porous structure may be found in Stokes, U.S. Pat. No. 4,506,680 and related Medtronic U.S. Pat. Nos. 4,577,642; 4,606,118 and 4,711,251 and in the Richter et al., U.S. Pat. No. 4,773,433; Heil Jr. et al., U.S. Pat. No. 4,819, 661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, all of which are incorporated herein in their entireties. It should be noted that, although electrodes 36, 37, 38, 39 of electrode array 28 are illustrated as annular rings, the scope of the present invention does not limit their geometry or arrangement within array 28.

Spacer elements 33 are preferably composed of a silicone rubber but may also be composed of a polyurethane, any other biocompatible and biostable insulative material, or a combination of these materials. Spacer elements 33 serve to both space and electrically isolate electrodes 36, 37, 38, 39 from one another.

Figures 4B, 4C:
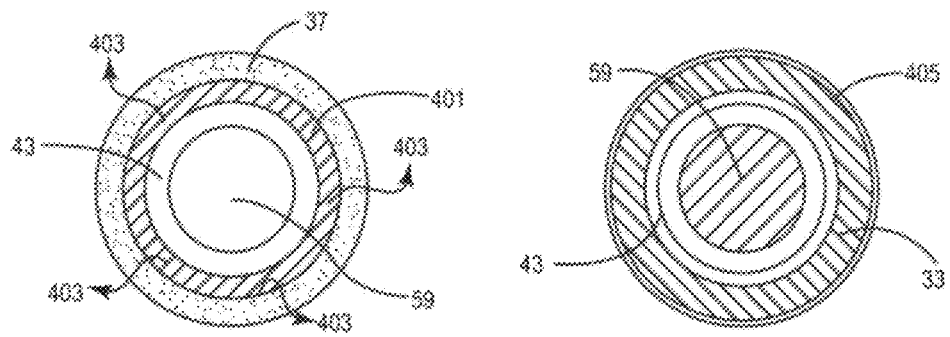

In addition, electrode array 28 preferably includes a means for steroid elution. FIGS. 4B-C are radial section views, through lines A-A and B-B, respectively, from FIG. 4A. As illustrated in FIG. 4B, a monolithic controlled release device (MCRD) 401, preferably constructed from silicone rubber and loaded with a derivative of dexamethasone, such as the water-soluble steroid dexamethasone sodium phosphate, is integrated into electrode array 28, coaxially positioned within electrode 37. MCRD 401 may be similarly positioned within any other electrode 36, 38, 39 or combination of electrodes 36, 37, 38, 39 of electrode array 28, or formed within tapered tip 34. Elution of steroid, depicted by arrows 403, is directed through a porous structure of electrode 37. MCRD construction and methods of fabrication are found in Stokes, U.S. Pat. No. 4,506,680 and related U.S. Pat. Nos. 4,577,642, 4,606, 118, and 4,711,251, which are incorporated herein in their entireties. Alternatively, as illustrated in FIG. 4C, a steroid coating 405 containing a no more than sparingly water-soluble steroid such as beclomethasone diproprionate or dexamethasone acetate may be applied to surfaces of one of the spacer elements 33 of electrode array 28. Coating 405 may be similarly applied to another spacer element 33 or a combination of spacer elements 33, or an electrode 36, 37, 38, 39, or a combination of electrodes 36, 37, 38, 39, or a combination of electrodes 36, 37, 38, 39 and spacer elements 33. A preferred embodiment of the present invention includes the steroid coating on surfaces of both spacer elements 33 and electrodes 36, 37, 38, 39 of electrode array 28 to maximize the probability for steroid contact near a selected site for pacing. The steroid coating is applied directly to the surfaces thus preserving their structural integrity and taking up less space than an MCRD or multiple MCRD's. A steroid coating composition and method of application is found in Williams, U.S. Pat. No. 5,987,746, which is incorporated herein in its entirety.

Figure 4D:
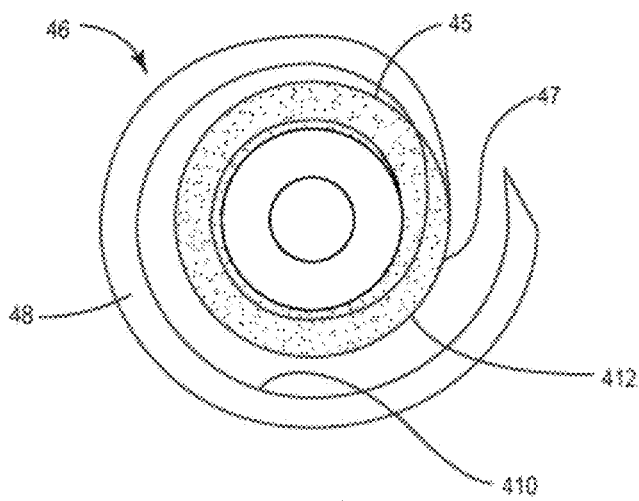

Fixation element 35 provides both a means for preventing dislodgement of electrode array 28 from implant site and a means for preventing over-insertion of electrode array 28 into an implant site. FIG. 4D is a distal end view from FIG. 4A. Referring now to FIGS. 4A and D, helical hook 46 includes a proximal portion 47 and a distal portion 48. Distal portion 48 extends out from collar 45 and spirals about lead body 32 for approximately one turn, as illustrated, or more turns, the number of turns not being limited by the scope of the present invention. As illustrated in FIG. 4D, an inner diameter 410 of distal portion 48 is greater than an outer diameter 412 of collar 45 so that distal portion 48 of helical hook 46 may engage tissue for fixation. Proximal portion 47 of helical hook 46 is embedded within collar 45 and spirals about lead body for approximately between one and five turns, the number of turns not being limited by the scope of the present invention. Collar 45 secures helical hook 46 to lead body 32 and provides a stop to prevent over insertion of electrode array 28 into tissue. Collar 45 is preferably composed of a biostable and biocompatible plastic or epoxy material capable of retaining attachment of helical hook 46 to lead body 32 via an adhesive bond and/or a mechanical interlock. Helical hook 46 is preferably composed of an MP35N alloy wire with a diameter between approximately 0.008 inches-0.012 inches. Although MP35N alloy is preferred other biocompatible and biostable materials such as a Pt/IR alloy, a tantalum, or a titanium may used to form helical hook 46. Fixation element 35 may also include a means for steroid elution, preferably as a coating on helical hook 46 similar to that described herein for electrode array 28.

In a preferred embodiment of the present invention electrodes 36, 37, 38, 39 each have a maximum outer diameter between approximately 0.040 inches and 0.060 inches and a length between approximately 0.040 inches-0.060 inches; spacer elements 33 each have a maximum outer diameter between approximately 0.040 inches and 0.060 inches and a length between approximately 0.060 inches-0.080 inches; and fixation element 35 has a maximum outer diameter between approximately 0.075 inches-0.085 inches with a distal edge 44 of collar 45 positioned between approximately 0.070 inches-0.090 inches proximal to a proximal edge 49 of most proximal electrode 36. Spacing of electrodes 36, 37, 38, 39 in electrode array 28 is tight enough to maintain discrete sensing of electrical activity within bundle of His zone 30, while maintaining electrical isolation between the electrodes. Array 28 is spaced from collar 45 of fixation element 35 to allow positioning of array 28 at a depth adequate for proximity to His zone 30 without perforating the heart wall.

Connector assembly 40 mates with an IPG connector module (not shown) and each contact 41 of connector assembly 40 correspond to an electrode of electrode array 28. When connector assembly 40 is joined to IPG connector module each contact 41 of connector assembly 40 engages with contacts of IPG connector module and each isolation zone 42 sealingly mates with isolation zones in IPG connector module. One, two or all electrodes of electrode array 28 may be selected for sensing and pacing; only those contacts of connector assembly 40, corresponding to selected electrodes, are electrically energized by IPG contacts. In a preferred embodiment connector assembly 40 has a maximum diameter between approximately 0.040 inches and 0.130 inches.

Multiple insulated conductors extending between connector assembly 40 and electrode array 28 within lead body 32 may be cables arranged co-linearly or coils arranged coaxially or individual filars of a single coil. In any of these configurations a lumen 43, shown with dashed lines in FIG. 4A, may be included in lead body 32. A stylet wire 59, shown with a bold dashed line, may be inserted into lumen 43, from a proximal end of connector assembly 40, in order to stiffen lead body 32 for insertion of electrode array 28 into tissue. According to the embodiment depicted in FIG. 4, a distal end of stylet would bottom out at a distal end 431 of lumen 43 within electrode 37 and may be used in pushing tapered tip 34 into tissue.

Figure 5:
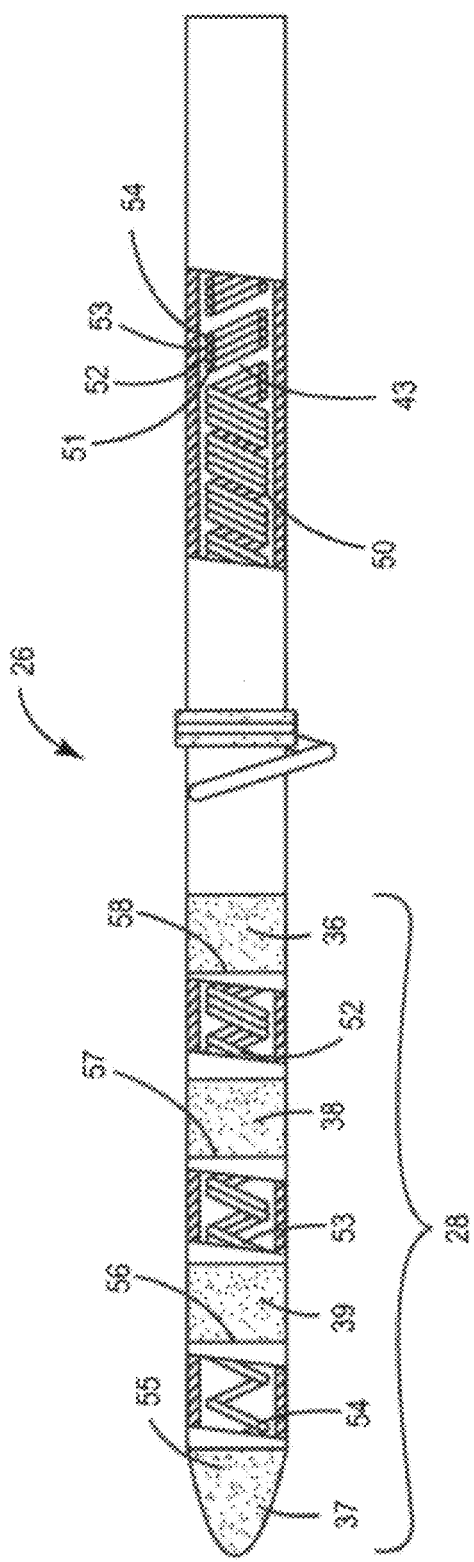
FIG. 5 is a plan view with partial section views of a distal portion of the Physiological pacing lead according to the present invention.

FIG. 5 is a plan view with partial section views of a distal portion of physiological pacing lead 26 according to the present invention. FIG. 5 illustrates a preferred embodiment for an arrangement of conductors as four filars 51, 52, 53, 54 in a coil 50. Lumen 43 is formed by an inner diameter of coil 50. Each filar 51, 52, 53, 54 is electrically coupled to an electrode in electrode array 28. Filar 51 is coupled to most proximal electrode 36 at a junction 58; filar 52 is coupled to intermediate electrode 38 at a junction 57; filar 53 is coupled to intermediate electrode 39 at a junction 56; and filar 54 is coupled to most distal electrode 37 at a junction 55. Junctions 55, 56, 57, 58 may be formed by welds or crimps, internally or externally, to electrodes 37, 38, 39, 36, respectively, such as is commonly known in the art.

Figure 6:
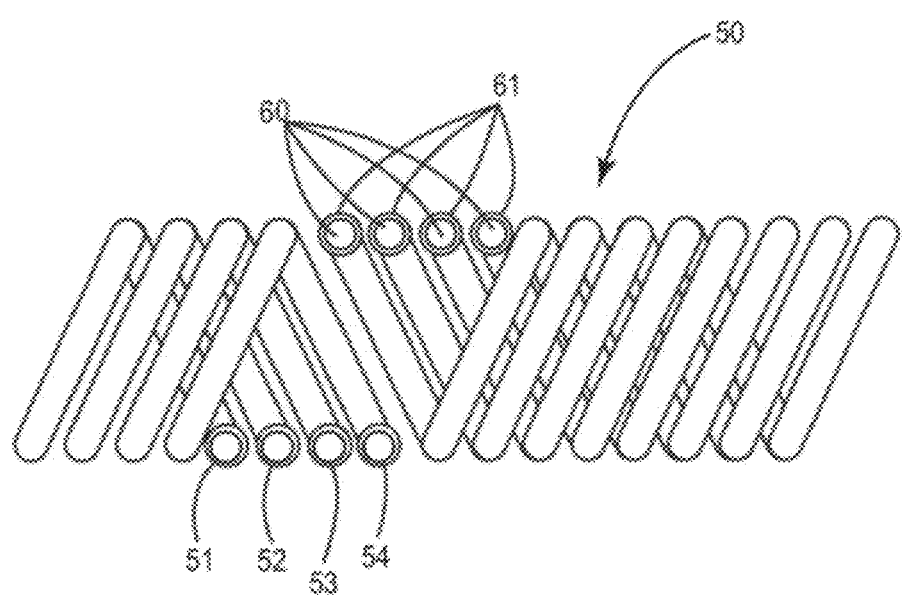
FIG. 6 is a detail view of a coil, enlarged from FIG. 5, with a partial section view.

FIG. 6 is a detail view of coil 50, enlarged from FIG. 5, with a partial section view. FIG. 6 illustrates each filar 51, 52, 53, 54 as separate isolated circuits defined by wires 60 surrounded by insulating layers 61. Preferably wires 60, having a diameter between approximately 0.003 inches and 0.007 inches, are composed of an MP35N alloy that is capable of reliably conducting electrical current after having been subjected to repeated bending and torsion loads, imposed by an implant environment, or any other material or combination of materials that is likewise capable. Preferably insulating layers 61 are composed of a durable, biocompatible and biostable polymer, such as ETFE.

Figure 7A:
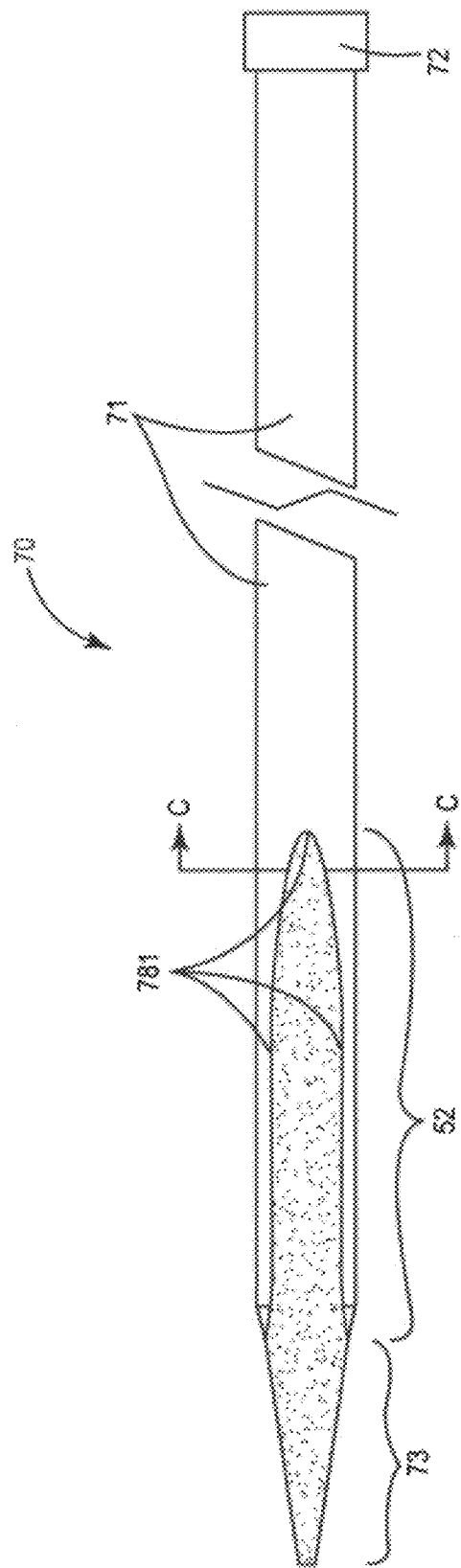
FIG. 7A is a top plan view of a piercing tool used to implant the electrode array of the Physiological pacing lead.
Figure 7C:
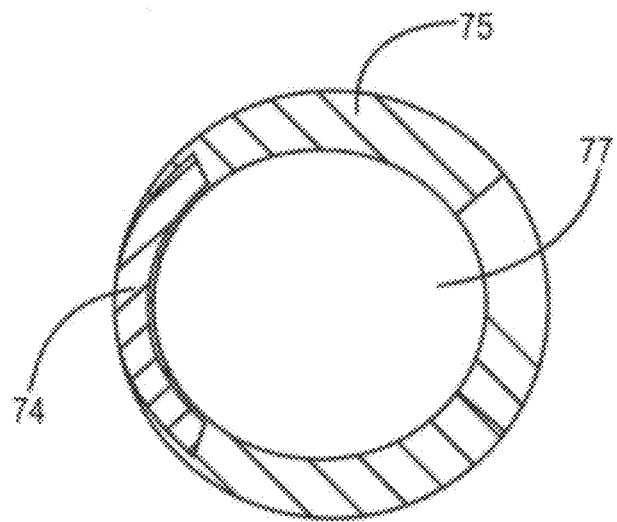
FIG. 7C is a radial section view from FIG. 7A.

FIG. 7A is a top plan view of a piercing tool 70 used to implant electrode array 28 of physiological pacing lead 26. As illustrated in FIG. 7A, piercing tool 70 includes an elongated hollow shaft 71 having a piercing tip 73 formed at a distal end and has a hub 72 terminating a proximal end. FIG. 7B is a cross-section side view of piercing tool 70 and FIG. 7C is a radial section view, section C-C from FIG. 7A. FIGS. 7B-C illustrate elongated hollow shaft 71 including a semi-rigid wall section 74, extending from hub 72 to a distal end of piercing tip 73, a flexible wall section 75, extending from hub 72 to a longitudinal recess 78, located proximal to distal end of piercing distal tip 73, and an inner lumen 77. Piercing distal tip 73 is terminated in a wedge 76. Semi-rigid wall section 74 transfers push forces from hub 72 to piercing distal tip 73 where wedge 76 initiates a piercing action to facilitate insertion of electrode array 28 into tissue. Portions 781, forming longitudinal recess 78, a purpose of which will be described in conjunction with FIG. 8, terminate flexible wall section 75.

According to the present invention, inner lumen 77 of hollow shaft 71 has a diameter between approximately 0.070 inches and 0.080 inches, to slideably receive lead body 32. A length of hollow shaft 71 is between approximately 15 inches and 25 inches, sufficient to engage an endocardial surface of RA 10 at a site adjacent to bundle of His 3 (FIGS. 1-2) from a cephalic or subclavian venous introduction site (not shown). Flexible wall section 75 is formed from a sufficiently flexible material, or combination of materials, to enable shaft 71 to track through venous system from an introduction site to a site adjacent to bundle of His 3 in RA 10, having a wall thickness between approximately 0.010 inches and 0.020 inches. Flexible wall section 75 may completely enclose or partially enclose semi-rigid wall section 74, the latter being illustrated in FIG. 7C. Semi-rigid wall section 74 is composed of a sufficiently rigid material to translate a push force from hub 72 to wedge 76 of piercing tip 73 and has a wall thickness between approximately 0.005 inches-0.010 inches.

FIG. 8A is a top plan view and FIG. 8B is a side elevation view of a distal portion of a physiological pacing delivery system 80 according to a preferred embodiment of the present invention. Delivery system 80 includes physiological pacing lead 26 and piercing tool 70. FIG. 8 illustrates an interface of electrode array 28 and fixation element 35 with piercing tip 73 and longitudinal recess 78. According to the present invention, distal piercing tip 73 extends a length 82 beyond a distal end 341 of tapered tip 34 that equals a longitudinal travel 81 between a distal end 481 of distal portion 48 of helical hook 46 and distal edge 44 of collar 45. Length 82 allows piercing tip 73 to bore deep enough into tissue for electrode array 28 to advance within the tissue as fixation element 35 is engaged into a surface of tissue, as further described below, in conjunction with FIG. 10B. Longitudinal recess 78 allows distal portion 48 of helical hook 46 to exit from lumen 77 of shaft 71 and spiral about shaft 71 and lead body 32 since an inner diameter 410 (FIG. 4D) of distal portion 48 is greater than an outer diameter 711 of shaft 71. Since distal portion 48 of helical hook 46 extends outward from lumen 77, diameter of lumen 77 only needs to be large enough, in a zone encompassing longitudinal recess 78, to accommodate an outer diameter of collar 45; as a result, shaft 71 may be slideably received within a catheter, used to guide delivery system 80 to an implant site, having a smaller diameter than a diameter that would be required if lumen 77 had to accommodated an outer diameter 411 (FIG. 4D) of helical hook 46.

Figure 9A:
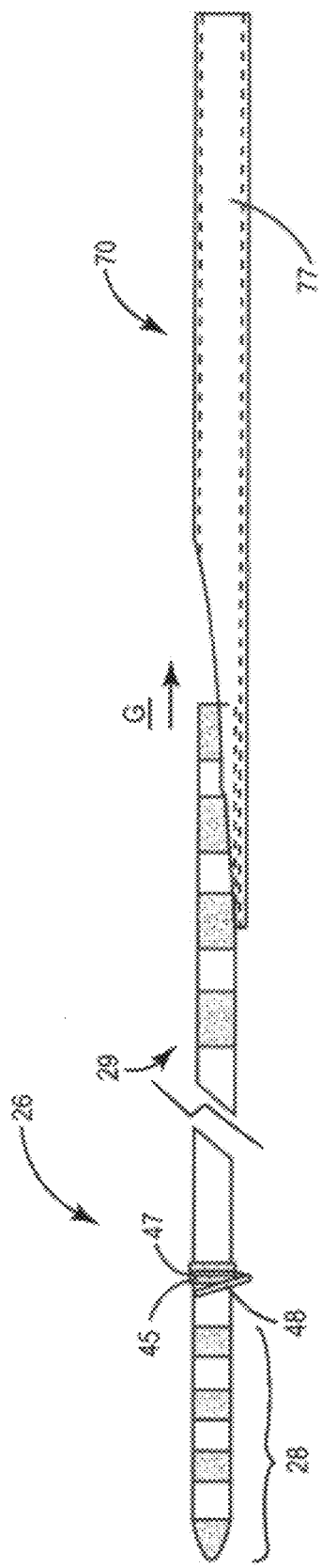
FIG. 9A is a side plan view of a means for assembling the delivery system.
Figure 9B:
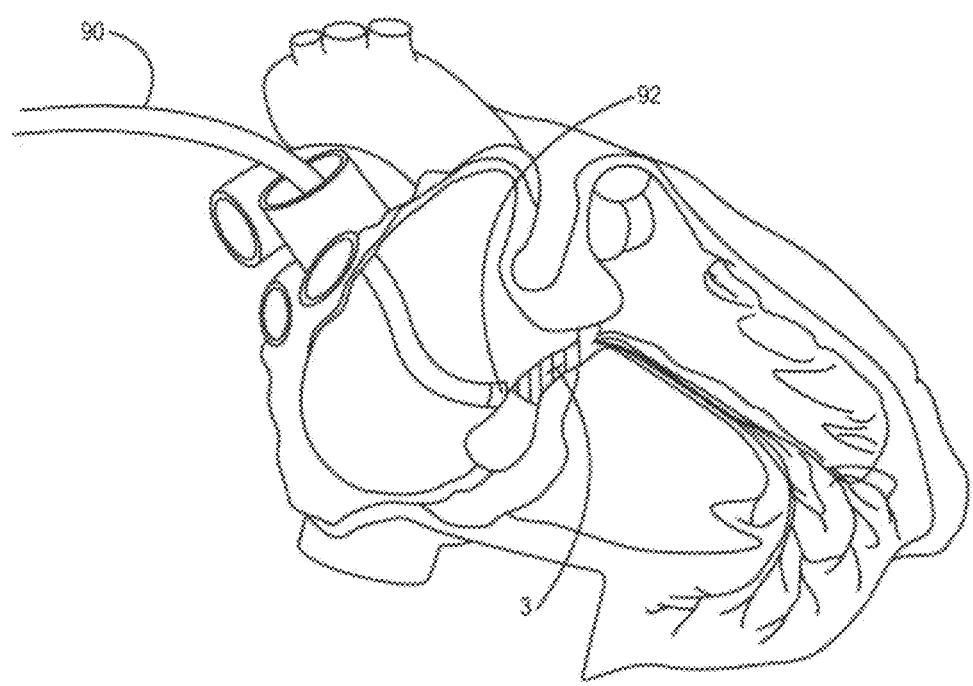
FIG. 9B is a schematic diagram of a right side of a heart, similar to FIG. 1, in which a guiding catheter is positioned for delivery of the physiological pacing lead.

FIG. 9A is a side plan view of a means for assembling delivery system 80. As illustrated in FIG. 9B, proximal end 29 of physiological pacing lead 26 is inserted, according to arrow G, into lumen 77 of piercing tool 70, at a distal end 701 of piercing tool 70, resulting in delivery system 80 illustrated in FIGS. 8A-B FIG. 9B is a schematic diagram of a right side of a heart, similar to that shown in FIG. 1, wherein a guide catheter 90 is positioned for delivery of physiological pacing lead 26. A venous access site (not shown) for guide catheter 90 may be in a cephalic or subclavian vein and means used for venous access are well known in the art, including the Seldinger technique performed with a standard percutaneous introducer kit. Guide catheter 90 includes a lumen (not shown) extending from a proximal end (not shown) to a distal end 92 that slideably receives delivery system 80. Guide catheter 90 may have an outer diameter between approximately 0.115 inches and 0.170 inches and is of a construction well known in the art. Distal end 92 of guiding catheter 90 may include an electrode (not shown) for mapping electrical activity in order to direct distal end 92 to an implant site near bundle of His 3. Alternatively a separate mapping catheter may be used within lumen of guide catheter 90 to direct distal end 92 to an implant site near bundle of His 3, a method well known in the art.

Figure 10A:
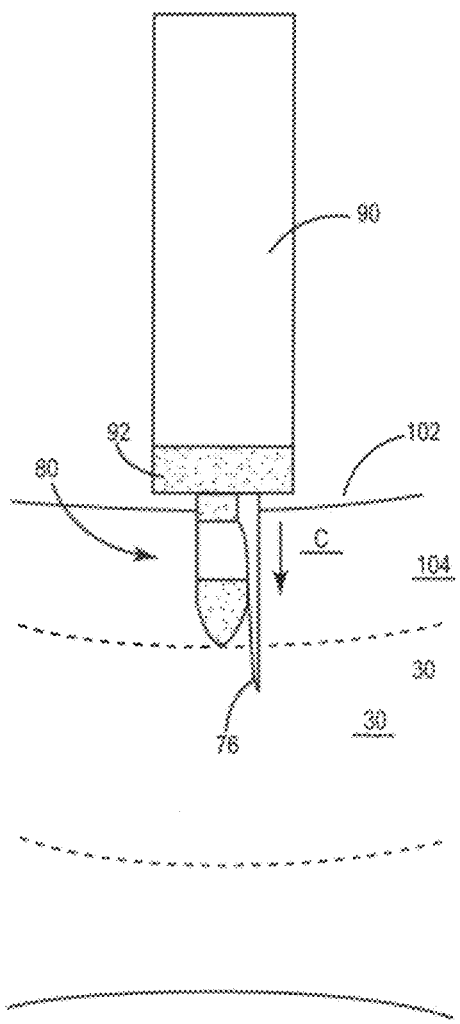
FIGS. 10A-B are schematic diagrams, with partial section, of the delivery system piercing a section of endocardial tissue having a bundle of His zone.
Figure 10B:
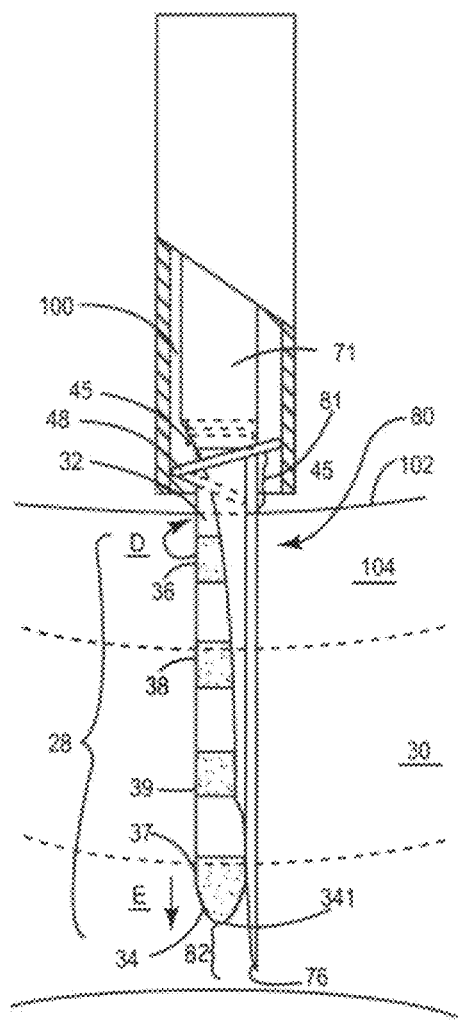

FIGS. 10A-B are a two-stage schematic diagram, with partial section, of delivery system 80 piercing a section of endocardial tissue 104 having bundle of His zone 30 (between dashed lines). FIGS. 10A-B illustrate guide catheter 90 positioned with distal end 92 against an RA endocardial surface 102 over endocardial tissue 104 encompassing bundle of His zone 30. A lumen 100 of guide catheter 90 slideably receives delivery system 80. In a first stage illustrated in FIG. 10A, arrow C defines the direction in which delivery system 80 is pushed to pierce surface 102 and penetrate His zone 30 with wedge 76 at distal end of piercing tool shaft 71. According to the present invention, delivery system 80 is fully inserted once distal portion 48 of helical hook 46 contacts surface 102, as illustrated in a second stage illustrated in FIG. 10B. Arrow D defines a rotation of lead body 32, initiated at proximal end 29 (FIG. 4A), in order to engage helical hook 46 with endocardial tissue 104; arrow E defines the travel of electrode array 28 as lead body 32 is rotated and helical hook 46 engages tissue 104. Length 81 is the longitudinal travel of helical hook, equal to length 82. Length 82, defining a gap between distal tip 76 and distal end 341 of tapered tip 34, allows piercing tip 73 to bore deep enough into tissue for electrode array 28 to advance within the tissue as fixation element 35 is engaged into a surface of tissue. Collar 45 prevents over-insertion of electrode array by butting up against endocardial surface 102. Arrow F defines a direction in which piercing tool shaft 71 and guide catheter 90 are pulled for removal. FIG. 3 defines implanted electrode array 28 of physiological pacing lead 26 after piercing tool 70 and guide catheter 90 are removed. Once electrode array 28 is implanted, every combination of electrodes, including 36, 37, 38, 39, and any additional electrodes, implanted either in the heart or subcutaneously, are energized to determine a first pair best suited for sensing and a second pair best suited for pacing. A first pair of electrodes, including, for example, electrodes 38 and 39, is selected based on a crispness and cleanness of a desired sensed signal. Alternatively first pair of electrode best suited for sensing may be on another implanted electrode array. A second pair of electrodes, including, for example, a subcutaneous electrode (not shown) and electrode 39, is selected based on a lowest threshold required to effectively stimulate bundle of His zone 30.

Figure 11A:
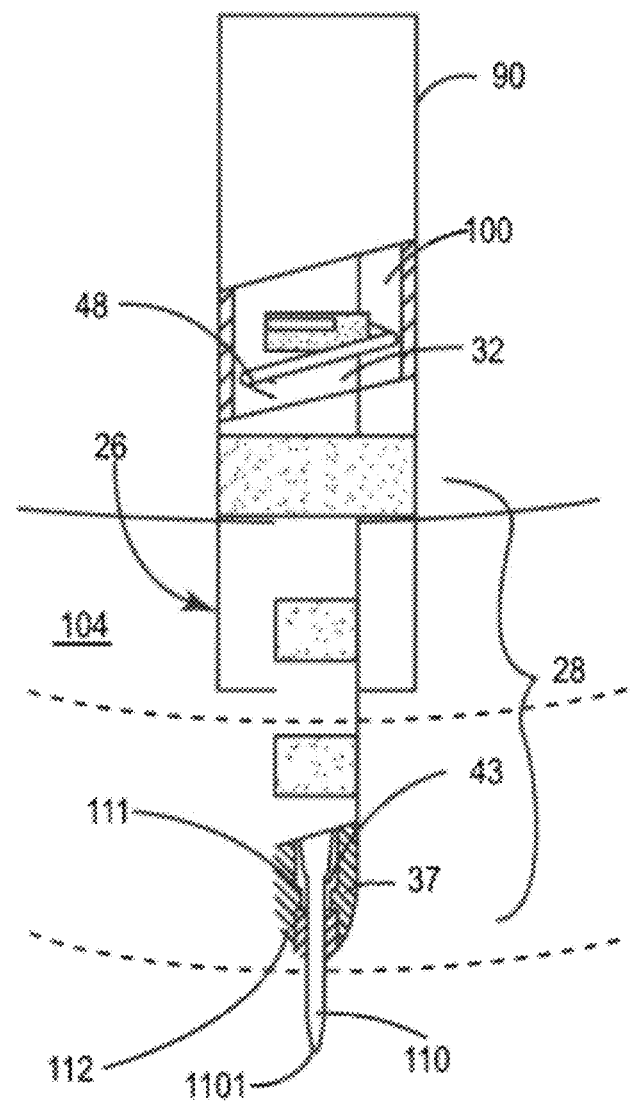
FIG. 11A is a schematic diagram, with partial section, of a stylet protruding from a tip element of the physiological pacing lead, piercing a section of endocardial tissue having a bundle of His zone.
Figure 11B:
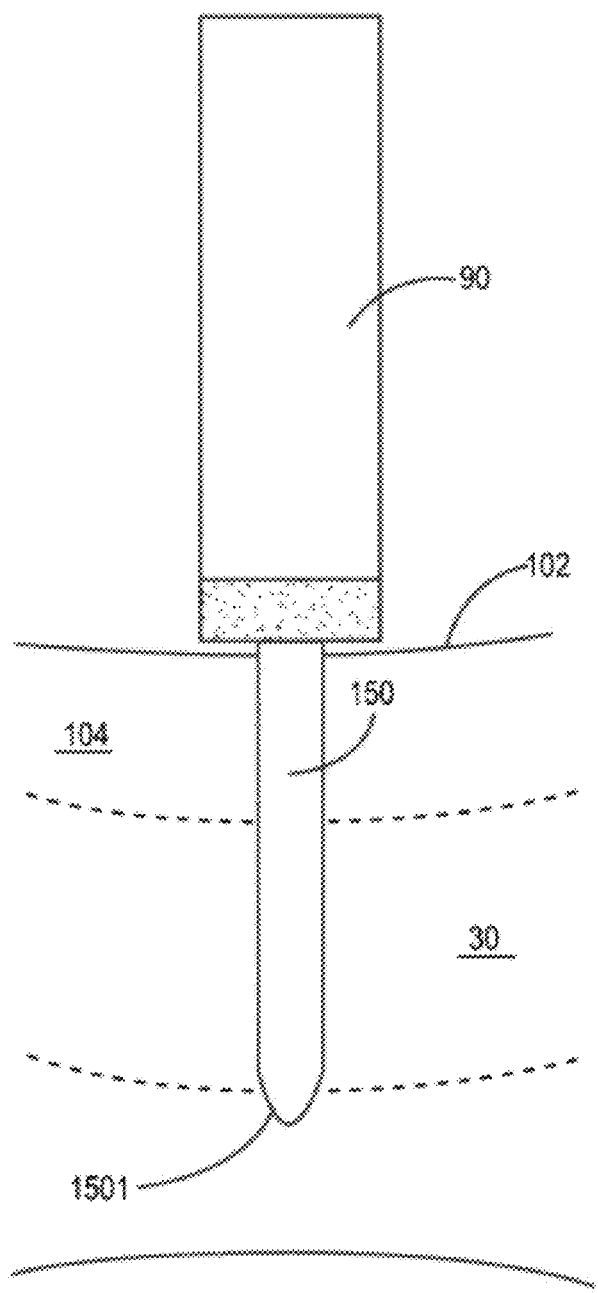
FIG. 11B is a schematic diagram illustrating an alternate piercing stylet.

FIG. 11A is a schematic diagram, with a cut-away view and a partial section, illustrating an alternate embodiment of a physiological pacing delivery system including a piercing stylet 110 according to the present invention. In this embodiment, physiological pacing lead 26 (FIG. 4) further includes a distal opening 111 having a seal member 112. Piercing stylet 110, having a piercing distal tip 1101 and being slideably disposed within lumen 43, may be advanced, through opening 111 and seal 112 to extend distally from most distal electrode 37 in order to pierce a section of endocardial tissue 104, thus facilitating insertion of electrode array 28 into tissue 104. Seal member 112 prevents entry of body fluid into lumen 43 as physiological pacing lead 26 is being delivered to implant site and after electrode array 28 has been implanted. Seal member 112 allows radial or lateral expansion as piercing stylet 110 is passed through seal member 112. Means for incorporating seal member 112 into physiological pacing lead 26 may be found in Sommer et al. U.S. Pat. No. 6,192, 280, which is incorporated in its entirety herein. FIG. 11B is a schematic diagram illustrating an alternate piercing stylet 150. Alternate piercing stylet 150, having a piercing tip 1501, is advanced through guide catheter 90 alone in order to create a bore in tissue 104 prior to inserting physiological pacing lead 26. Either piercing stylet 110 or alternate piercing stylet 150, as compared to piercing tool 70 (FIGS. 7-10), will allow for a smaller diameter guide catheter since a maximum diameter of helical hook 48 does not need to be large enough to spiral around piercing tool shaft 71 as depicted in FIGS. 8 and 10.

Figure 12:
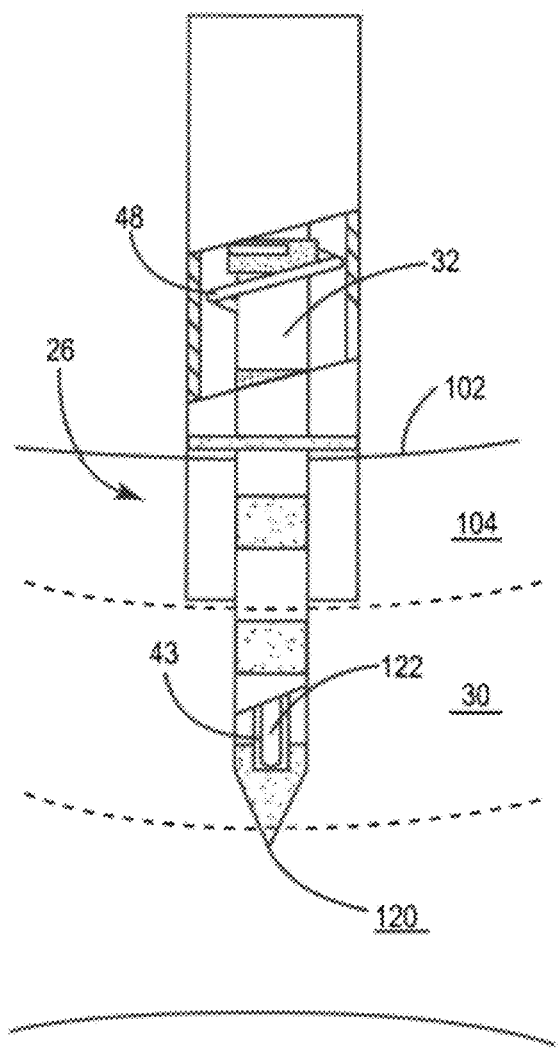
FIG. 12 is a schematic diagram, with cut-away view and a partial section, illustrating yet another alternative embodiment of a physiological pacing delivery system according to the present invention.

FIG. 12 is a schematic diagram, with cut-away view and a partial section, illustrating yet another alternative embodiment of a physiological pacing delivery system according to the present invention. In this embodiment, physiological pacing lead 26 (FIG. 4) further includes a piercing tip 120. A stylet 122, slideably disposed within lumen 43 serves to both stiffen lead body 32 and to push piercing tip 120 into endocardial tissue 104. In this manner, a bore is created for electrode array 28 by piercing tip 120. This embodiment may allow for a smaller diameter guide catheter since a maximum diameter of helical hook 48 does not need to be large enough to spiral around piercing tool shaft 71 as depicted in FIGS. 8A-B and 10A-B.

Figure 13A:
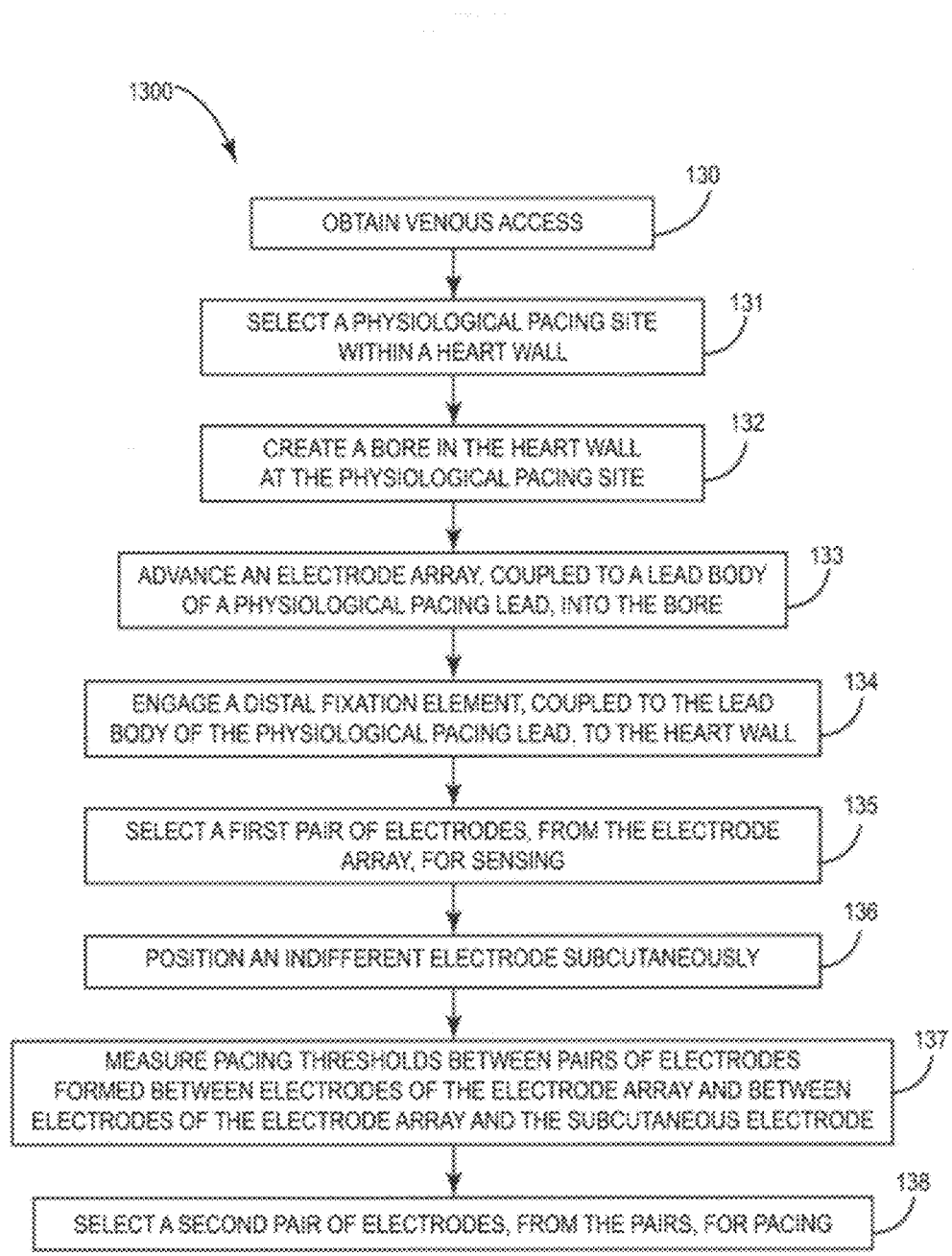
FIGS. 13A-E are flow charts illustrating sequences of steps included in alternate methods for implanting a physiological pacing lead.

FIG. 13A is a flow chart of a general method 1300 for implanting electrode array 28 of physiological pacing lead 26. Implanting method 1300 of the present invention, illustrated by FIG. 13A, may be followed using any of the embodiments of delivery systems disclosed herein. Starting at a step 130, means used to obtain venous access are well known in the art, and include the Seldinger technique performed with a standard percutaneous introducer kit. A physiological pacing site is selected, step 131, by knowledge of cardiac conduction pathways and visualization of a patient's cardiac anatomy, and may include electrical mapping via guide catheter 90. (Reference FIG. 9.) A bore is created in a heart wall at the physiological pacing site, step 132, by any one of the piercing tips of systems disclosed herein, including that of piercing tool 70, that of piercing stylet 110, that of alternate piercing stylet 150, and that of physiological pacing lead 26. (Reference FIGS. 7-10, 11, and 12, respectively.) Electrode array 28 coupled to lead body 32 is advanced into the bore, step 133. Distal fixation element 35, coupled to lead body 32, is engaged, by rotation of lead body 32, to heart wall to complete an implant of electrode array 28, step 134. (Reference FIG. 10.) Steps 135-138 result in a selection of first and second pair of electrodes, as described above in conjunction with FIG. 10B, to be used for pacing therapy.

Figure 13B:
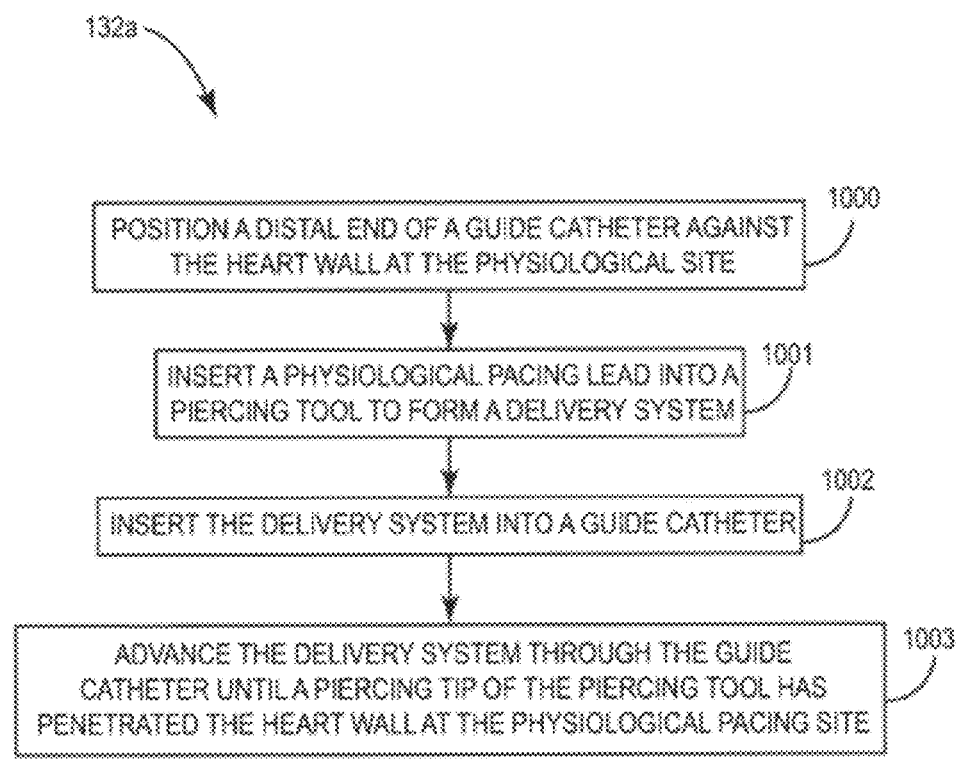
Figure 13C:
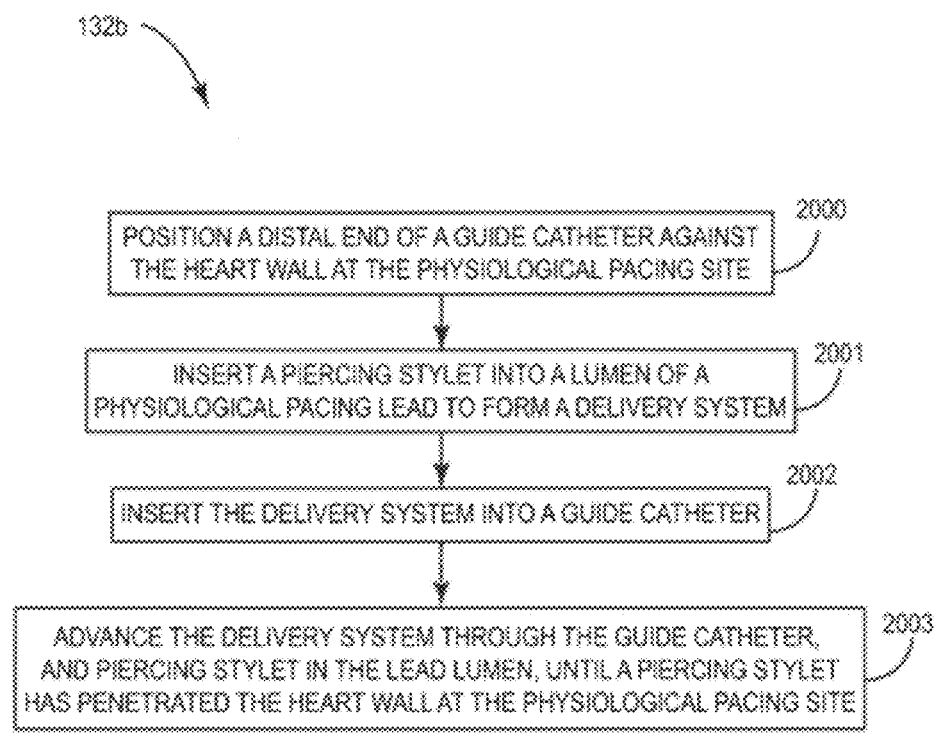
Figure 13D:
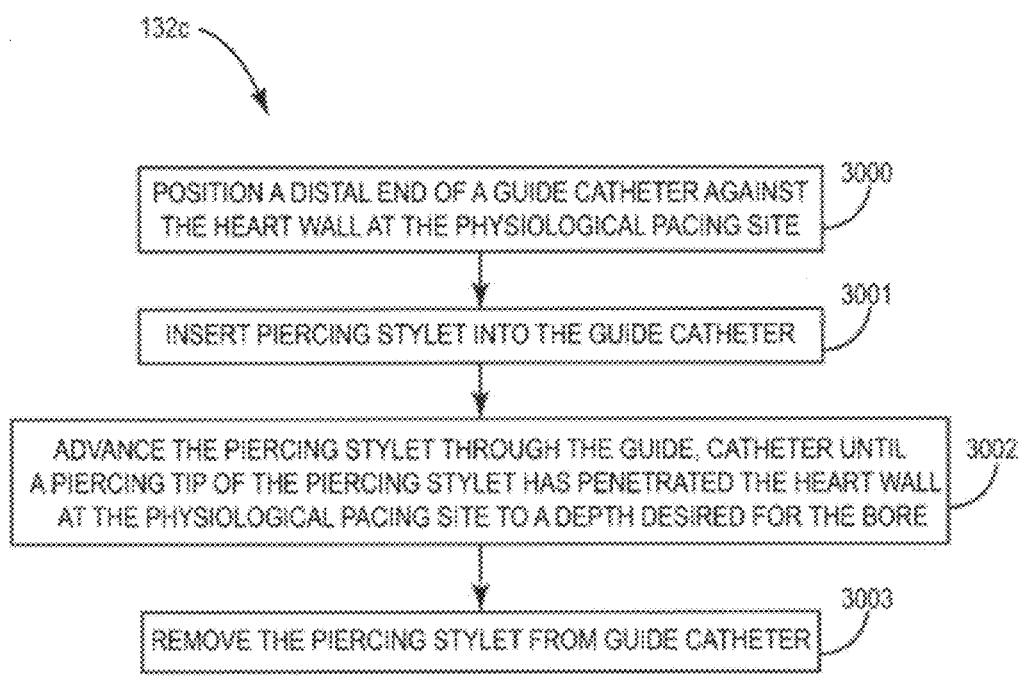
Figure 13E:
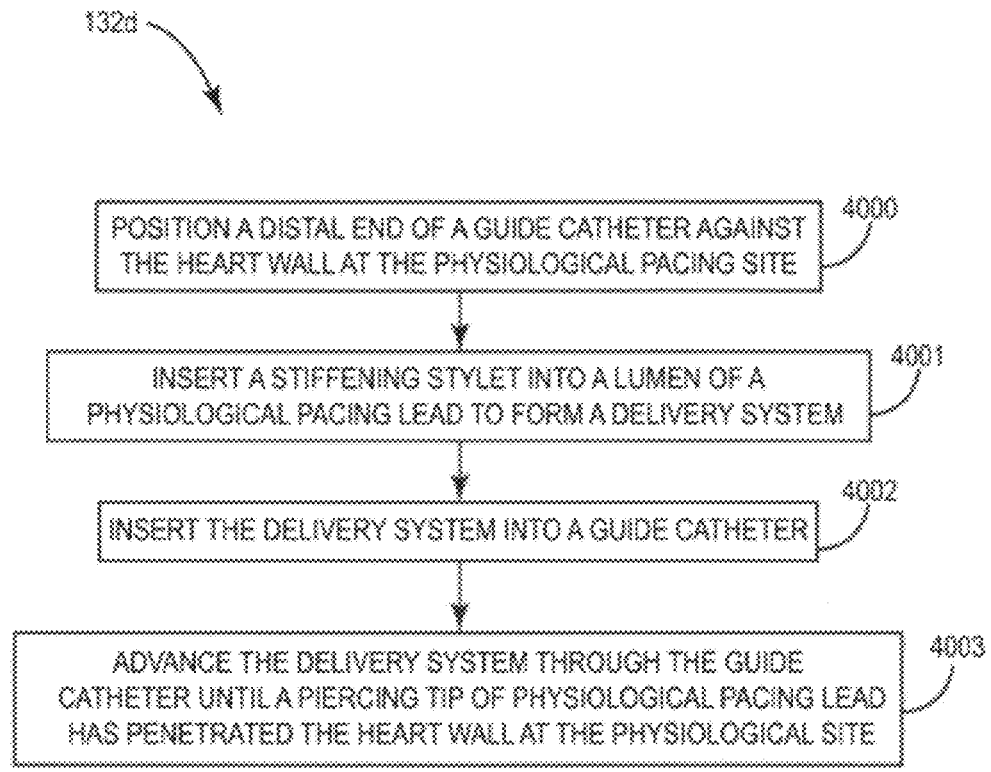

FIGS. 13B-E are flow charts of alternative methods defining step 132 of method 1300 of FIG. 13A and associated with each one of the piercing tips disclosed herein. FIG. 13B illustrates a method 132a associated with piercing tool 70. Once distal end 92 of guide catheter 90 has been positioned, step 1000, and physiological pacing lead 26 has been inserted into piercing tool 70 to form delivery system 80, step 1001, delivery system 80 is inserted into guide catheter 90 and advanced until piercing tip 73 of piercing tool 70 has penetrated at the physiological pacing site, steps 1002-1003. FIG. 13C illustrates a method 132b associated with piercing stylet 110. Once distal end 92 of guide catheter 90 has been positioned, step 2000, and piercing stylet 110 has been inserted into lumen 43 of physiological pacing lead 26 to form a delivery system, 2001, delivery system is inserted into guide catheter 90 and advanced until a piercing tip of piercing stylet 110 has penetrated at the physiological pacing site, steps 2002-2003. FIG. 13D illustrates a method 132c associated with alternate piercing stylet 150. Once distal end 92 of guide catheter 90 has been positioned, step 3000, piercing stylet 150 is inserted into guide catheter 90 and advanced to create a bore at physiological pacing site, steps 3001-3002. Once the bore is made, alternate piercing stylet 150 is removed from guide catheter, step 3003. FIG. 13E illustrates a method 132d associated with piercing tip 120 of physiological pacing lead 26. Once distal end 92 of guide catheter 90 has been positioned, step 4000, and stiffening stylet 59 has been inserted into lumen 43 of physiological pacing lead 26 to form a delivery system, step 4001, delivery system is inserted into guide catheter 90 and advanced until piercing tip 120 of physiological pacing lead 26 has penetrated at the physiological pacing site, steps 4002-4003.

Figure 14:
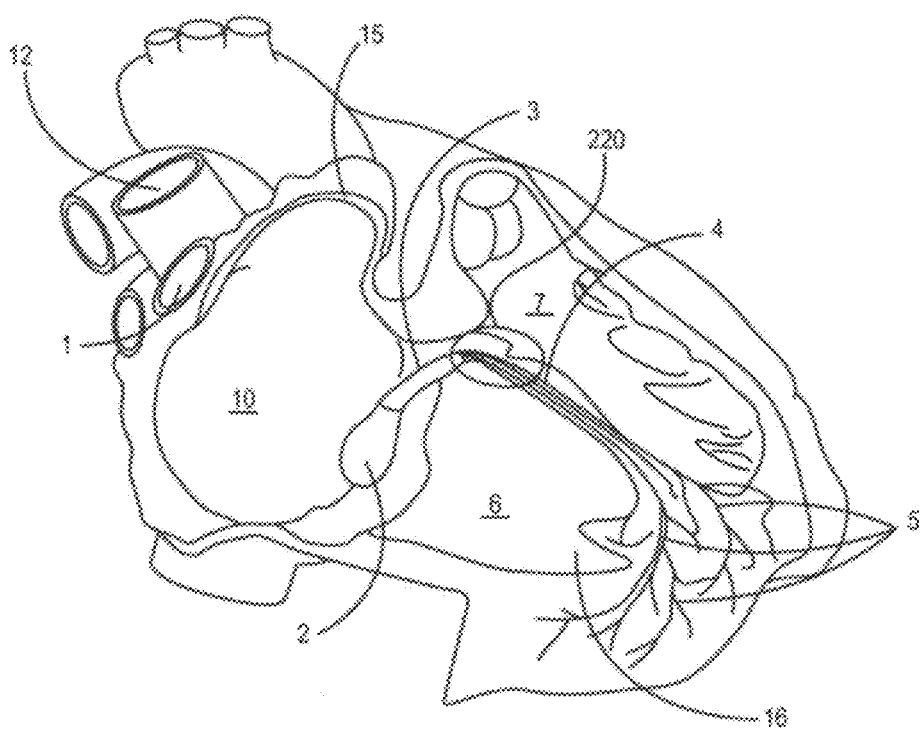
FIG. 14 is a schematic diagram of a right side of a heart, similar to FIG. 1.

Pacing leads similar to lead 26 previously described, were used to investigate sites in proximity to the bundle of His in order to determine electrode implant locations most suitable for physiological pacing. A zone 220 within interventricular septum 7, as illustrated in FIG. 14, was found to be one in which pacing stimulation results in a rhythm breaking out at an intrinsic location, i.e. that of a normal sinus rhythm. Rhythm breakout locations were determined by characterizing activation patterns and conduction properties observed during sinus and paced rhythms via non-contact mapping using the EnSite™ 3000 Workstation commercially available from Endocardial Solutions.

Within zone 220 physiological pacing may be further optimized for good detection of ventricular activity and relatively efficient pacing. According to a method of the present invention, one or a pair of electrodes are inserted into zone 220 and positioned such that the following criteria are met:

a. a ratio of an amplitude of sensed atrial electrical activation (P-wave amplitude) to an amplitude of sensed ventricular activation (R-wave amplitude) is less than approximately 0.5 resulting in good detection of ventricular activity (i.e. clear discrimination between atrial and ventricular activation); and b. a pacing threshold is less than or equal to approximately 1.5 volts resulting in relatively efficient pacing.

Figure 15:
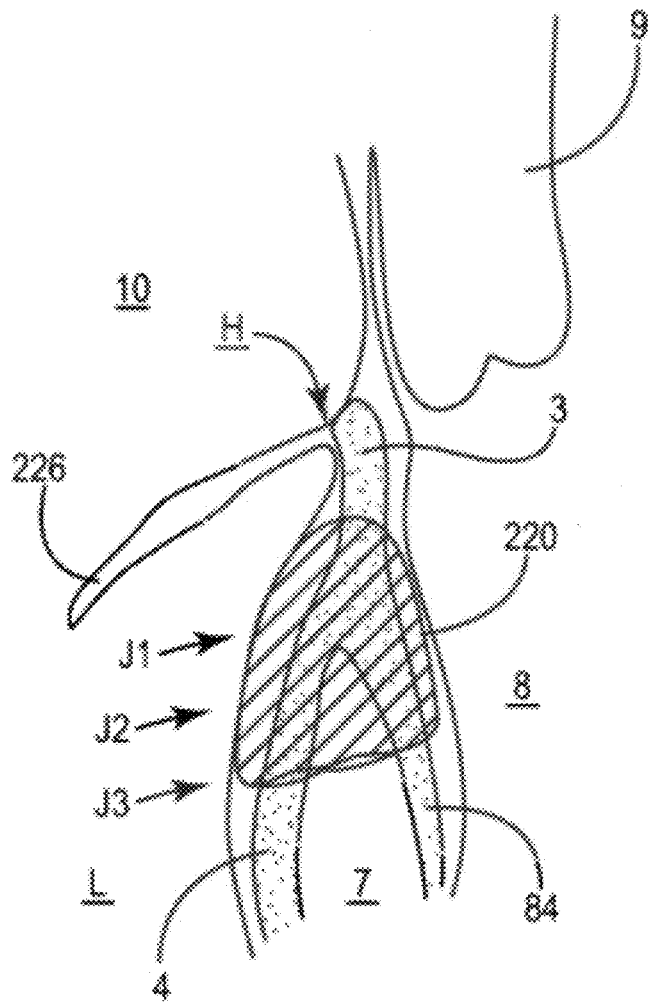
FIG. 15 is a section view of a portion of the heart depicted in FIG. 14.

FIG. 15 is a section view of a portion of the heart depicted in FIG. 14 illustrating alternate avenues for inserting electrodes into zone 220. According to one method of the present invention a single electrode or a pair of electrodes are advanced through atrium 10 to be inserted into zone 220 per arrow H, while according to another method the single electrode or pair of electrodes are advanced through atrium 10, past a tricuspid valve 226, and into ventricle 6 to be inserted per one or all of arrows J1-3. The single electrode or pair of electrodes is positioned at various points within zone 220 either by varying an insertion depth or by changing an insertion site, i.e. arrows J1-3, or by selecting from an array of electrodes, i.e. array 28 previously described, spanning a depth of insertion. According to yet another method zone 220 may be reached via an epicardial approach as previously described in conjunction with FIG. 2.

Figure 16A:
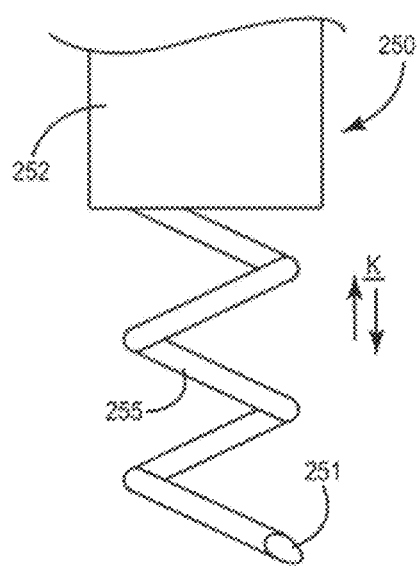
FIGS. 16A-B are plan views of distal portions of alternative pacing leads.
Figure 16B:
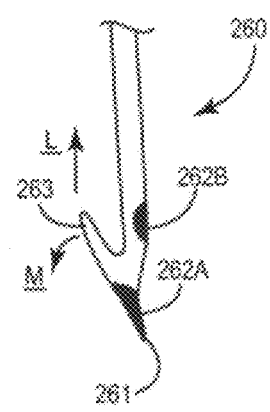

FIGS. 16A-B are plan views of distal portions of alternative pacing leads which may be used to practice methods of the present invention. FIG. 16A illustrates a pacing lead 250 including a helical electrode 255 extending distally from a distal end 252; helical electrode 255 includes a piercing tip 251 facilitating insertion into zone 220 and a geometry of electrode 255 serves to anchor electrode 255 within zone 220. Helical electrode 255 may be fixed to distal end 252 such that the entire lead 250 must be rotated to insert electrode into zone 220 or electrode 255 may be extendable and retractable per arrows K into and out from distal end 252, via rotation of an inner drive shaft; both embodiments are well known to those skilled in the art. Selecting a depth of electrode 255 in zone 220 is particularly facilitated by the extendable-retractable embodiment. FIG. 16B illustrates a pacing lead 260 including an alternate embodiment including a distal end 40 having a harpoon-like geometry for anchoring of electrodes 262A-B within zone 220. FIG. 16B further illustrates electrode 262A including a piercing tip 261 facilitating insertion of electrodes 262A-B and an anchoring tine 263 extending proximally from electrode 262A. According to this illustrated embodiment, after electrodes 262A-B are inserted into zone 220 to an appropriate depth, wherein the pacing criteria previously described are met, lead 260 is pulled back slightly per arrow L to deploy tine 263 per arrow M. It should be noted that lead 26, along with any of the associated tools previously described, may also be used to practice methods of the present invention.

In the foregoing detailed description, the invention has been described with reference to specific embodiments. However, it may be appreciated that various modifications and changes can be made without departing from the scope of the invention as set forth in the appended claims.

What is claimed is:

1. A method, comprising:
   inserting at least one electrode into cardiac tissue in proximity to a portion of an intrinsic conduction system of a patient's heart;
   measuring, using the at least one electrode, a P-wave amplitude and an R-wave amplitude;
   determining a ratio of the P-wave amplitude to the R-wave amplitude;
   measuring a pacing threshold using the at least one electrode,
   selecting an electrode implant site based at least on the ratio of the P-wave amplitude to the R-wave amplitude and the measured pacing threshold;
   positioning an electrode at the selected electrode implant site for sensing cardiac signals; and
   sensing a cardiac signal using the electrode positioned at the selected electrode implant site.

2. The method of claim 1, further comprising:
   inserting the at least one electrode at various points in proximity to the portion of the intrinsic conduction system; and
   determining the ratio of the P-wave amplitude to the R-wave amplitude for each of the various points.

3. The method of claim 2, wherein inserting the at least one electrode at various points comprises varying an insertion depth of the at least one electrode.

4. The method of claim 3, wherein the at least one electrode comprises an extendable and retractable electrode and wherein varying an insertion depth comprises advancing the extendable and retractable electrode to various depths within the cardiac tissue.

5. The method of claim 2, wherein inserting the at least one electrode at various points comprises changing an insertion site of the at least one electrode.

6. The method of claim 1, wherein inserting the at least one electrode comprises inserting a plurality of electrodes in proximity to a portion of the intrinsic conduction system, the method further comprising:
   measuring a P-wave amplitude and an R-wave amplitude for each of the plurality of electrodes; and
   determining a ratio of the P-wave amplitude to the R-wave amplitude for each of the plurality of the electrodes.

7. The method of claim 1, wherein measuring a pacing threshold further comprises measuring a pacing threshold using the at least one electrode when pacing stimulation results in a rhythm breaking out in the intrinsic conduction system, and further wherein the method comprises:
   positioning an electrode at the selected electrode implant site for pacing; and
   delivering physiological pacing using the electrode positioned at the selected electrode implant site for pacing.

8. The method of claim 7, wherein selecting the electrode implant site comprises selecting an electrode implant site for sensing and for pacing;
   the electrode implant site being selected based at least on the ratio of the P-wave to R-wave amplitude determined for the electrode implant site exceeding a predetermined ratio threshold and the pacing threshold measured for the electrode implant site being no greater than a predetermined pacing threshold.

9. The method of claim 8, wherein the predetermined ratio threshold being approximately 0.5 and the predetermined pacing threshold being approximately 1.5 volts.

10. The method of claim 1, wherein inserting the at least one electrode comprises advancing the at least one electrode endocardially into cardiac tissue.

11. The method of claim 1, wherein inserting the at least one electrode comprises advancing the at least one electrode epicardially into cardiac tissue.

12. A method, comprising:
    inserting an electrode pair into cardiac tissue in proximity to a portion of an intrinsic conduction system of a patient's heart;
    positioning the electrode pair at various points in proximity to the portion of the intrinsic conduction system;

measuring, using the electrode pair, a P-wave amplitude and an R-wave amplitude at each of the various points;

determining a ratio of the P-wave amplitude to the R-wave amplitude;

measuring a pacing threshold using at least one electrode of the electrode pair;

selecting an electrode implant site based at least on the ratio of the P-wave amplitude to the R-wave amplitude and on the measured pacing threshold;

positioning the electrode pair at the selected electrode implant site for sensing cardiac signals; and sensing a cardiac signal using the electrode pair positioned at the selected electrode implant site.

13. The method of claim 12, wherein positioning the electrode pair at various points comprises varying an insertion depth of the electrode pair.

14. The method of claim 12, wherein inserting the electrode pair at various points comprises changing an insertion site of the electrode pair.

15. The method of claim 12, wherein inserting the electrode pair comprises inserting an array of electrodes in proximity to a portion of the intrinsic conduction system, the method further comprising:

measuring a P-wave amplitude and an R-wave amplitude for electrode pairs selected from the array of electrodes; and determining a ratio of the P-wave amplitude to the R-wave amplitude for each of the electrode pairs.

16. The method of claim 12, wherein measuring the pacing threshold further comprises measuring a pacing threshold using at least one electrode out of the electrode pair when pacing stimulation results in a rhythm breaking out in the intrinsic conduction system, and further wherein the method comprises:

positioning an electrode at the selected electrode implant site for pacing; and delivering physiological pacing using the electrode positioned at the selected electrode implant site for pacing.

17. The method of claim 16, wherein selecting the electrode implant site comprises selecting an electrode implant site for sensing and for pacing, the electrode implant site being selected based at least on the P-wave amplitude to R-wave amplitude ratio determined for the electrode implant site exceeding a predetermined ratio threshold and the pacing threshold measured for the electrode implant site being no greater than a predetermined pacing threshold.

18. The method of claim 17, wherein the predetermined ratio threshold being approximately 0.5 and the predetermined pacing threshold being approximately 1.5 volts.

19. The method of claim 12, wherein inserting the electrode pair comprises advancing the electrode pair endocardially into cardiac tissue.

20. The method of claim 12, wherein inserting the electrode pair comprises advancing the electrode pair epicardially into cardiac tissue.

* * * * *